United States Patent [19]
Gabriel et al.

[11] Patent Number: 5,702,467
[45] Date of Patent: Dec. 30, 1997

[54] PATELLAR RESURFACING COMPONENT

[75] Inventors: Stefan M. Gabriel, Lakeville; David G. Sheehan, Carver, both of Mass.

[73] Assignee: Johnson & Johnson Professional, Inc., Raynham, Mass.

[21] Appl. No.: 660,970

[22] Filed: Jun. 12, 1996

[51] Int. Cl.$^6$ .................................. A61F 2/30; A61F 2/38
[52] U.S. Cl. ............................................ 623/20; 623/18
[58] Field of Search ................................ 623/20, 18

[56] References Cited

U.S. PATENT DOCUMENTS

| | | | |
|---|---|---|---|
| 4,158,894 | 6/1979 | Worrell | 623/20 |
| 4,240,162 | 12/1980 | Devas | 3/1.91 |
| 4,344,192 | 8/1982 | Imbert | 3/1.91 |
| 4,964,867 | 10/1990 | Boger | 623/20 |
| 4,979,957 | 12/1990 | Hodorek | 623/20 |
| 5,019,104 | 5/1991 | Whiteside et al. | 623/20 |
| 5,197,986 | 3/1993 | Mikhail | 623/20 |
| 5,236,462 | 8/1993 | Mikhail | 623/20 |
| 5,246,460 | 9/1993 | Goodfellow et al. | 623/20 |
| 5,383,937 | 1/1995 | Mikhail | 623/20 |
| 5,480,443 | 1/1996 | Elias | 623/18 |

FOREIGN PATENT DOCUMENTS

| | | | |
|---|---|---|---|
| 2700260 | 7/1994 | France | 623/20 |
| 2009601 | 6/1979 | United Kingdom | 623/20 |
| 9213503 | 8/1992 | WIPO | 623/20 |
| 9422397 | 10/1994 | WIPO | 623/20 |

*Primary Examiner*—Debra S. Brittingham
*Assistant Examiner*—Tram Anh T. Nguyen
*Attorney, Agent, or Firm*—Susan M. Schmitt

[57] ABSTRACT

A patellar component is provided for fixation to a patella and a total knee arthroplasty surgical procedure in which multiple surfaces are provided on an outer ring on the inferior surface of the patellar component to provide multi-directional load bearing surfaces available to resist loosening of the patellar component and which requires minimal bone removal for implantation.

4 Claims, 4 Drawing Sheets

PATELLAR RESURFACING COMPONENT

FIELD OF THE INVENTION

The present invention relates to an inset patellar component of a prosthetic knee implant for use in patellar resurfacing.

BACKGROUND OF THE INVENTION

The patellar component in total knee arthroplasty replaces a degenerated patellar articular surface to articulate with a femoral component. Presently two general methods of patellar component implantation are typically used. In the first group ("resurfacing"), the patellar component is placed onto a planed surface of the natural patella, relying on pegs which protrude into the patellar bone for resistance to shear loads parallel to the planed surface and tensile compressive loads perpendicular to the planed surface. The second group, is the "inset" patellar component type which is typically countersunk into the bone of a natural patella in a recessed cavity.

Although each of these types of patellar component implants have been used with general success in implant procedures, the patellar components now used may be susceptible to loosening of the component within the bone due to loss of interlock between the cement and the prosthesis. For example, a decrease in the amount of interlock between the component and bone cement may occur when a central articular load is applied to a typical known patellar component. This is classically described as the Poisson effect which describes the deformation of a material in directions perpendicular to an applied load. Also, implantation procedures using these devices have required removal of a substantial amount of bone in order to provide adequate fixation within the patella.

Accordingly, it is desirable to provide a patellar component with improved fixation to the natural patella. It is also desirable to provide an implant that will decrease "Poisson" type loosening. It is further desirable to provide a patella prosthesis that may be used in both resurfacing or and inset type procedures. It is also desirable to provide a patellar component that will require removal of less bone than when using the components now typically used.

It is also desirable in providing secure attachment of the components to maintain contact between the bone cement and the prosthesis under varying load conditions that may effect such contact.

SUMMARY OF THE INVENTION

Accordingly, the present invention provides a patella component with features on the inferior (non-articulating) surface of the patellar component to allow for positive interlocking between component and cement for a multitude of loading conditions. The patellar component may either be positioned on a planed surface with pegs extending into a bored surface, or recessed in a counter-bored cavity in the patella. The patella may be used in either resurfacing or inset procedures.

One feature of the invention provides a raised undercut surface generally facing away from the central axis. It is believed that this undercut surface, among other things, acts to increase the interlock between the component and bone cement, holding it more firmly in place when outward expansion of the component occurs. Also in one embodiment a raised undercut surface generally facing towards a central axis is provided in addition to the raised undercut surface facing away from the axis.

In a preferred embodiment, a central peg acts as a centralizing element that is arranged to resist both shear and tension. The central peg defines a central axis having an axis vector in a direction going from the articular surface to the bone interface of the patella implant. A plane perpendicular to the vector axis roughly defines interfacing surface.

Another feature of the invention provides interlocking surfaces at varying distances from the central axis on the plane of the inferior prosthetic patella surface or on a plane approximately perpendicular to the central axis.

In one embodiment a curved ring extends around the outer circumference of the patella component. The ring is provided with a curved geometry having surfaces to resist torsional loads around the peg axis. The ring is raised from the inferior surface of the patellar component and undercuts are made in the curved ring to provide an interlocked surface available to resist loosening of the patellar component. The undercut features are oriented both generally toward and away from the central peg. The raised ring has surfaces alternatingly convex and concave with respect to the central peg that curve around the ring inner and outer circumferences to alternate the distance of the inner and outer circumferences from the central peg.

In an alternative embodiment a plurality of pegs are used instead of a single centrally located peg.

In another embodiment a plurality of raised surfaces are formed around the axis of the patellar component.

DETAILED DESCRIPTION OF THE DRAWINGS

DETAILED DESCRIPTION OF THE DRAWINGS

Figure 1:
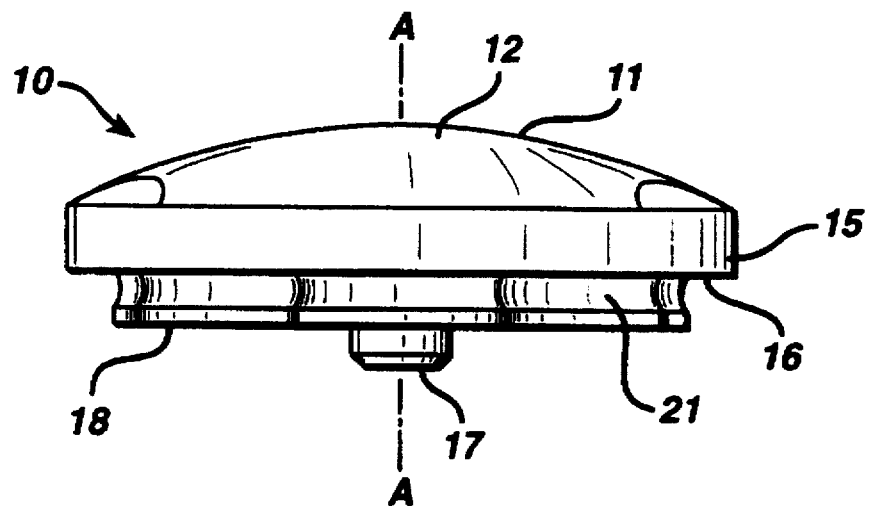
FIG. 1 is a side view of the patellar component of the present invention.
Figure 2:
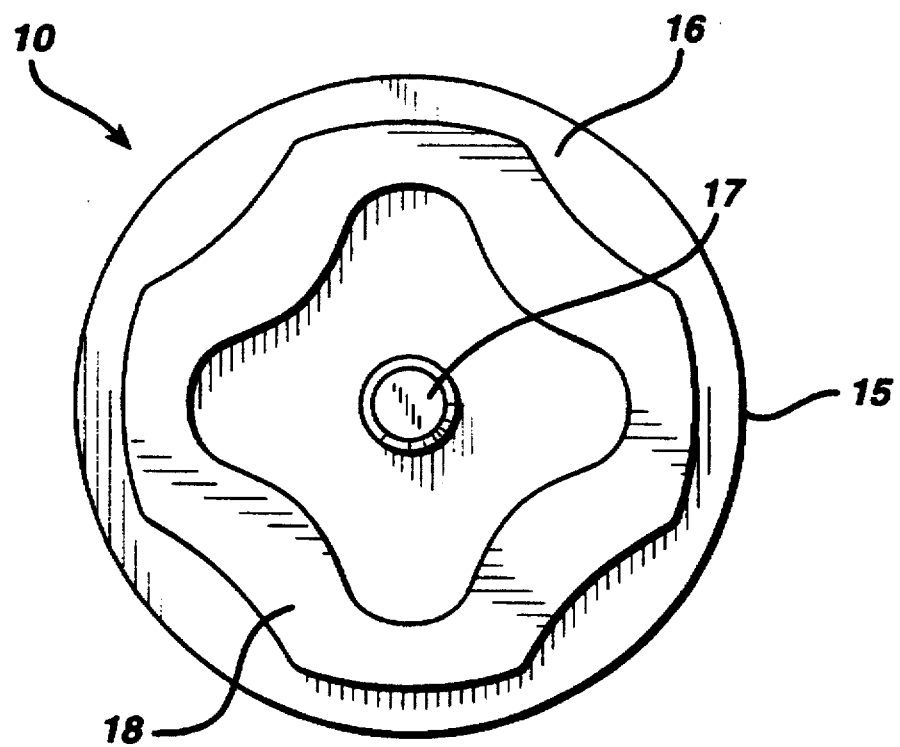
FIG. 2 is a view of the patellar component of the present invention.
Figure 3:
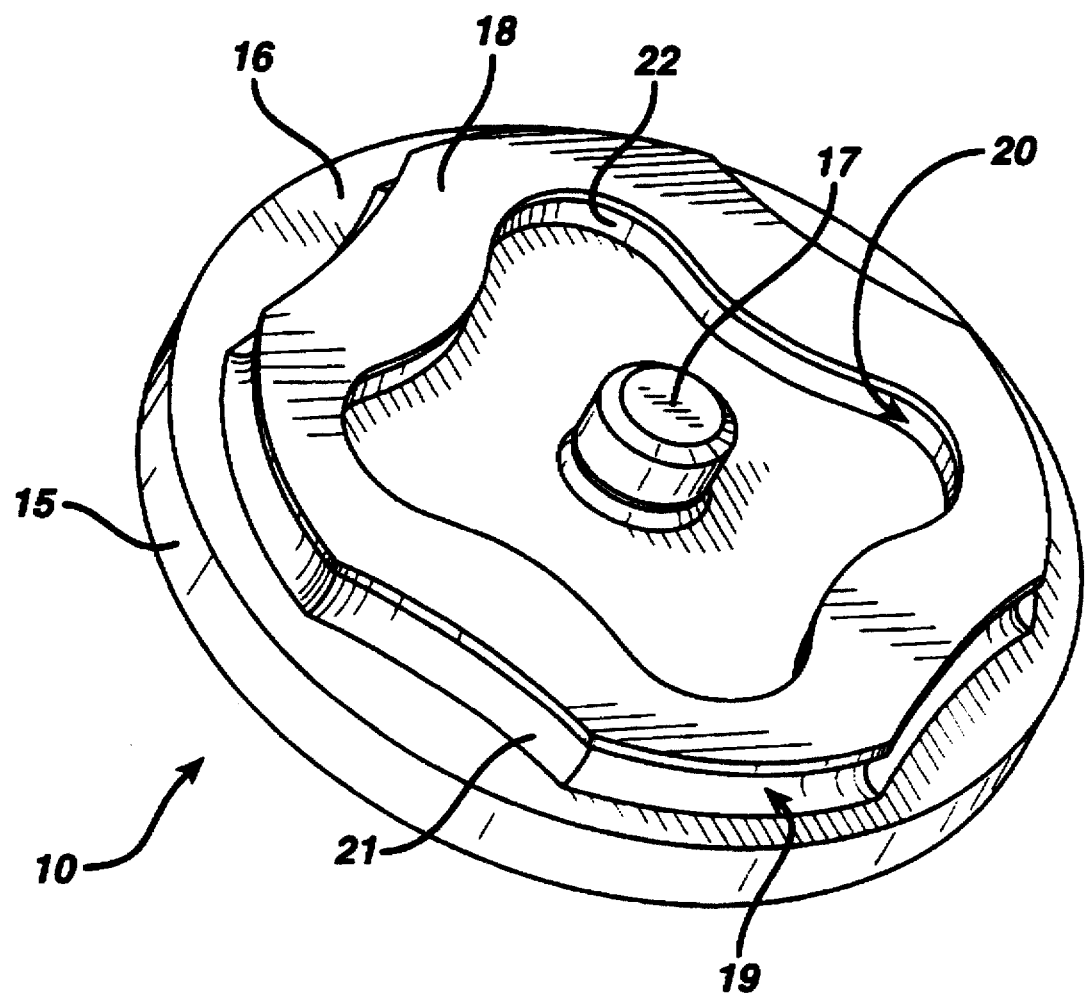
FIG. 3 is a perspective view illustrating the inferior surface of the patellar component of FIG. 2.

Referring now to FIGS. 1–4 there is illustrated a patellar component 10 of the present invention. The patellar component 10 is preferably comprised of all polyethylene and is machined as one piece. The patellar component 10 comprises a superior spherical sector 12 having a spherical articulating surface 11 shaped to articulate with a trochlear groove of a femoral component. The patellar component 10 further comprises an inferior surface 16 for fixing or locking the patella to the patellar component 10, and a cylindrical mid section 15 which joins the superior spherical sector 12 to the inferior surface 16.

The inferior surface 16 comprises a central peg 17 for centralizing and supporting the patella component in a prepared cavity. The peg 17 defines an axis A—A, generally perpendicular to the plane of the inferior surface 16 and extending through superior and inferior surfaces 11, 16. The inferior surface 16 further comprises a raised ring 18 comprising an outer sidewall 19 and an inner sidewall 20. The outer sidewall 19 extends generally around the outer circumference of the raised ring 18 while the inner sidewall 20 extends around the inner circumference of the raised ring 18. The inner wall 20 has an undercut surface 22 generally facing the central peg. The outer wall 19 has an undercut surface 21 generally facing away from the peg. The undercut surfaces are concave on a plane parallel to the central axis. The outer wall 19 is alternatingly concave and convex about the outer circumference with respect to the inner central peg 17, i.e., on a plane perpendicular to the central axis. The inner wall 20 also is alternatingly convex and concave about the inner circumference of the ring with respect to the central peg 17.

The central peg 17 acts primarily as a centralizing feature but also helps to resist shear. The surfaces 21, 22 are intended to resist loosening of the component by allowing cement interlocking on both sides of the ring 18 and to provide resistance at different angles with respect to the axis and at varying distances from the central peg 17. The undercuts of the inner and outer wall surfaces as well as the alternating concave and convex orientation of the walls with respect to the central peg 17 are intended to allow for positive interlocking between component and cement for a wide variety loading conditions. The undercuts in the curved ring 18 are oriented to provide such interlocking regardless of the direction of loading, or the expansion/contraction of the patella from loads, etc. The curved geometry of the ring is also intended to help resist torsional loads around the peg axis.

In use a patella 43 is prepared by either planing or reaming the patella 43 depending on the geometry of the implant and whether a standard or inset type patella is to be used. The circular symmetry of the design allows a single reaming operation to be used for preparation of a natural patella for implantation of component. Once the patella 43 is prepared using means generally known in the art, the patellar component 10 is cemented in place. The joint 40 is reduced after all the implant components are in place and the patella component 10 is then able to articulate with the femoral component 30.

Figure 4:
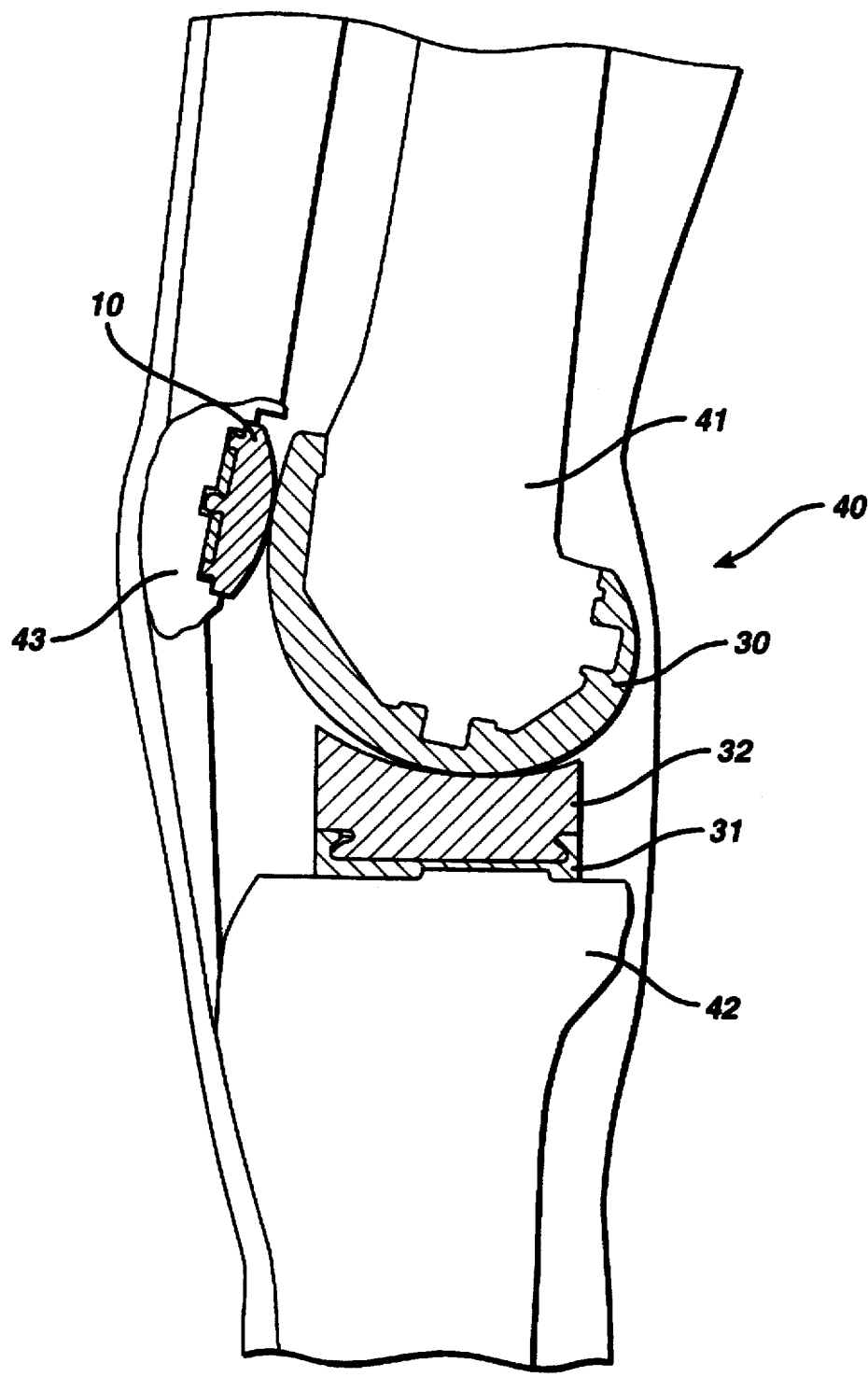
FIG. 4 is an illustration of the patellar component of the present invention implanted in a patella and placed in a patient with a prosthetic knee implant.

FIG. 4 illustrates a knee joint 40 comprising a femur 41, tibia 42 and patella 43. A tibial tray 31 with bearing insert 32 is implanted into the tibia 42. A femoral component 30 is implanted in the femur 41. The femoral component 30 articulates with the bearing surface 32 of the tibia and the patella component 10 articulates with the femoral component 30.

Figure 5:
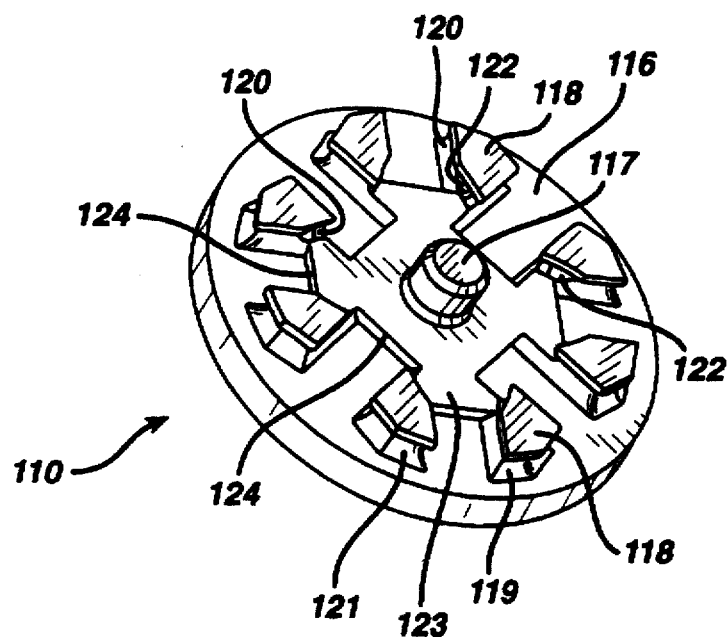
FIG. 5 is a perspective view illustrating the inferior surface of an alternative embodiment of the present invention.

Referring now to FIG. 5, an alternative embodiment is illustrated comprising patellar component 110 with inferior surface 116 for fixing or locking the patellar component 110 to the patella.

The inferior surface 116 comprises a central stem 117 and raised elements 118. Each raised element 118 comprises inner side walls 120 and outer side walls 119. The inner side walls 120 have undercut surfaces 122 generally facing the central stem 117. Each inner side wall 120 is oriented at a different angle with respect to the central stem 117 to provide alternative load bearing characteristics of the interlocking surfaces. Each outer side wall 119 has an undercut surface 121 generally facing away from the central stem 117. Each outer side wall 119 is oriented at a different angle with respect to the central shaft 117 to provide a variety of alternative load bearing surfaces at different angles. The inferior surface 116 further comprises a central raised surface 123 located around the central stem 117 and connecting the raised elements 118 with raised walls 124 which provide a continuous surface in combination with outer side walls 119. The central raised surface 123 is raised to a lesser degree than the raised elements 118 thus allowing inner walls 120 to provide load bearing contact with cement and bone.

Figure 6:
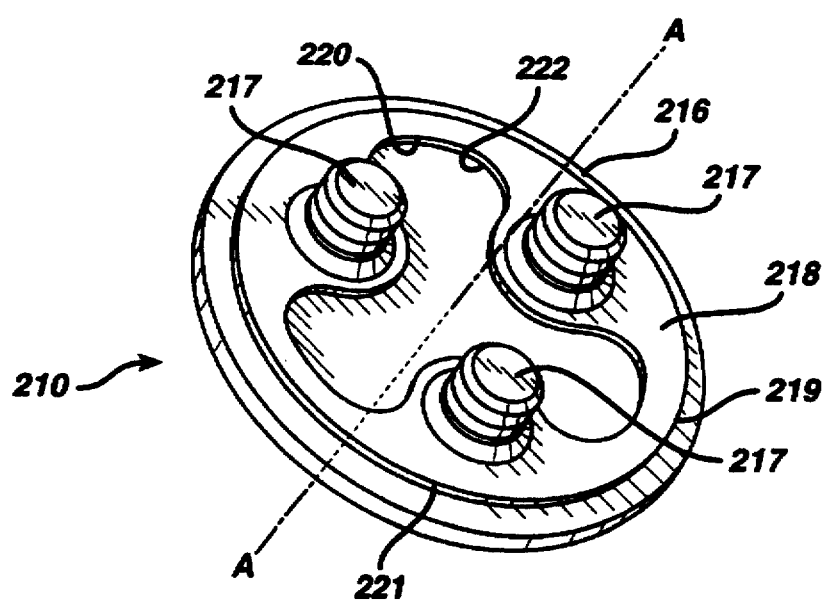
FIG. 6 is a perspective view illustrating the inferior surface of another alternative embodiment of the present invention.

Referring now to FIG. 6, a second alternative embodiment is illustrated comprising patellar component 210 with inferior surface 216 for fixing or locking the patellar component 210 to the patella.

The inferior surface 216 comprises pegs 217 for centralizing and supporting the patellar component 210 in a prepared cavity. The inferior surface 216 further comprises a raised ring 218 comprising an outer sidewall 219 and an inner sidewall 220. The outer sidewall 219 extends generally around the outer circumference of the raised ring 218 while the inner sidewall 220 extends around the inner circumference of the raised ring 218. The implant 210 has an axis, generally perpendicular to the plane of the interior surface 216. The inner wall 220 has an undercut surface 222 generally facing the central axis. The outer wall 219 has an undercut surface 221 generally facing away from the central axis A—A, to resist loosening of the component by allowing cement interlocking on both sides of the ring and to provide resistance at different angles with respect to the axis and at different distances from the central peg. The outer wall 219 is alternatingly concave and convex about the outer circumference with respect to the central axis A—A. The inner wall 220 also is alternatingly convex and concave about the inner circumference of the ring with respect to the central axis A—A.

The embodiments illustrated in FIGS. 5 and 6 may be used in a similar manner as the patella implant in FIGS. 1–4.

Although the present invention is described with reference to specific embodiments, it should be understood by those skilled in the art that numerous equivalents and modifications may be made without departing from the scope and spirit of the invention.

We claim:

1. A patellar prosthesis comprising:
   a body having:
   a convexly shaped articular surface for articulating with a femoral prosthesis; and
   an inferior surface for interfacing with a patella bone to couple said patellar prosthesis to a prepared patella bone, said inferior surface comprising:
   a central axis extending from said articular surface through said inferior surface;
   a raised portion comprising a first undercut surface, said first undercut surface facing away from said axis; and
   a second undercut surface, said second undercut surface facing toward said axis; wherein said first undercut surface is a first radial distance from said axis and said second undercut surface is a second radial distance from said axis; and
   wherein said first distance is greater than said second distance.

2. A patellar prosthesis comprising:
   a body having:
   a convexly shaped articular surface for articulating with a femoral prosthesis; and
   an inferior surface for interfacing with a patella bone to couple said patellar prosthesis to a prepared patella bone, said inferior surface comprising:
   a central axis extending from said articular surface through said inferior surface;

a raised portion comprising a first undercut surface, said first undercut surface facing away from said axis; and a central peg located on said axis;

wherein said raised portion comprises a ring concentric with said central peg.

3. The prothesis of claim 2 wherein said raised portion is alternatingly concave and convex with respect to said axis on a plane generally perpendicular to said axis.

4. A patellar prosthesis comprising:

a body having:

a convexly shaped articular surface for articulating with a femoral prosthesis; and an inferior surface for interfacing with a patella bone to couple said patellar prosthesis to a prepared patella bone, said inferior surface comprising:

a central axis extending from said articular surface through said inferior surface;

a raised portion comprising a first undercut surface, said first undercut surface facing away from said axis; and a second undercut surface, said second undercut surface facing toward said axis; and a plurality of pegs;

wherein said raised portion comprises a ring extending circumferential around said plurality of pegs.

* * * * *